(12) United States Patent
Bettencourt

(10) Patent No.: US 10,060,921 B2
(45) Date of Patent: Aug. 28, 2018

(54) METHODS OF TREATING TRANSTHYRETIN (TTR) MEDIATED AMYLOIDOSIS

(71) Applicant: Alnylam Pharmaceuticals, Inc., Cambridge, MA (US)

(72) Inventor: Brian Bettencourt, Groton, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/507,691

(22) PCT Filed: Aug. 27, 2015

(86) PCT No.: PCT/US2015/047185
§ 371 (c)(1),
(2) Date: Feb. 28, 2017

(87) PCT Pub. No.: WO2016/033326
PCT Pub. Date: Mar. 3, 2016

(65) Prior Publication Data
US 2017/0307608 A1    Oct. 26, 2017

Related U.S. Application Data

(60) Provisional application No. 62/044,100, filed on Aug. 29, 2014, provisional application No. 62/150,596, filed on Apr. 21, 2015.

(51) Int. Cl.
| | | |
|---|---|---|
| *C12N 15/11* | (2006.01) | |
| *G01N 33/566* | (2006.01) | |
| *C07D 263/57* | (2006.01) | |
| *G01N 33/50* | (2006.01) | |
| *G01N 33/53* | (2006.01) | |
| *G01N 33/567* | (2006.01) | |
| *G01N 33/68* | (2006.01) | |
| *C07K 1/00* | (2006.01) | |
| *C12N 15/113* | (2010.01) | |

(52) U.S. Cl.
CPC ......... *G01N 33/566* (2013.01); *C07D 263/57* (2013.01); *G01N 33/50* (2013.01); *G01N 33/53* (2013.01); *G01N 33/567* (2013.01); *G01N 33/6896* (2013.01); *C07K 1/00* (2013.01); *C12N 15/113* (2013.01)

(58) Field of Classification Search
None
See application file for complete search history.

(56) References Cited

U.S. PATENT DOCUMENTS

| | | | |
|---|---|---|---|
| 7,250,496 B2 | 7/2007 | Bentwich | |
| 7,427,605 B2 | 9/2008 | Davis et al. | |
| 7,718,629 B2 | 5/2010 | Bumcrot et al. | |
| 7,834,170 B2 | 11/2010 | Khvorova et al. | |
| 8,168,775 B2 | 5/2012 | Sah et al. | |
| 8,741,866 B2 | 6/2014 | Sah et al. | |
| 9,101,643 B2 | 8/2015 | Sah et al. | |
| 9,228,186 B2 | 1/2016 | Khvorova et al. | |
| 9,234,196 B2 | 1/2016 | Sah et al. | |
| 2002/0160394 A1 | 10/2002 | Wu | |
| 2003/0072794 A1 | 4/2003 | Boulikas | |
| 2003/0143732 A1 | 7/2003 | Fosnaugh et al. | |
| 2003/0170891 A1 | 9/2003 | McSwiggen | |
| 2003/0229037 A1 | 12/2003 | Massing et al. | |
| 2004/0259247 A1 | 12/2004 | Tuschl et al. | |
| 2005/0244869 A1 | 11/2005 | Brown-Driver | |
| 2005/0276804 A1 | 12/2005 | Smith et al. | |
| 2006/0008910 A1 | 1/2006 | MacLachlan et al. | |
| 2006/0083780 A1 | 4/2006 | Heyes et al. | |
| 2006/0135460 A1 | 6/2006 | Widder et al. | |
| 2006/0240093 A1 | 10/2006 | MacLachlan et al. | |
| 2006/0263435 A1 | 11/2006 | Davis et al. | |
| 2007/0004664 A1 | 1/2007 | McSwiggen et al. | |
| 2007/0031844 A1 | 2/2007 | Khvorova et al. | |
| 2007/0135372 A1 | 6/2007 | MacLachlan et al. | |
| 2007/0207974 A1 | 9/2007 | Khvorova et al. | |
| 2007/0281899 A1 | 12/2007 | Bumcrot et al. | |
| 2008/0188675 A1 | 8/2008 | Chen et al. | |
| 2009/0023215 A1 | 1/2009 | Jessee et al. | |
| 2009/0023673 A1 | 1/2009 | Manoharan et al. | |
| 2009/0082300 A1 | 3/2009 | Brown-Driver et al. | |
| 2009/0149403 A1 | 6/2009 | MacLachlan | |
| 2009/0247608 A1 | 10/2009 | Manoharan et al. | |
| 2009/0291131 A1 | 11/2009 | MacLachlan et al. | |
| 2010/0120893 A1 | 5/2010 | Sah et al. | |
| 2010/0130588 A1 | 5/2010 | Yaworski | |
| 2010/0324120 A1 | 12/2010 | Chen et al. | |
| 2011/0015250 A1 | 1/2011 | Bumcrot et al. | |

(Continued)

FOREIGN PATENT DOCUMENTS

| | | |
|---|---|---|
| WO | WO 2004/045543 | 6/2004 |
| WO | WO 2004/080406 | 9/2004 |

(Continued)

OTHER PUBLICATIONS

Akinc, A. et al., "A Combinatorial Library of Lipid-Like Materials for Delivery of RNAi Therapeutics," Nature Biotechnology. 26(5), Apr. 27, 2008, pp. 561-569.

(Continued)

*Primary Examiner* — Ekaterina Poliakova-Georgantas
(74) *Attorney, Agent, or Firm* — Fenwick & West LLP

(57) ABSTRACT

Disclosed herein are methods for reducing or arresting an increase in a Neuropathy Impairment Score (NIS) or a modified NIS (mNIS+7) in a human subject by administering an effective amount of a transthyretin (TTR)-inhibiting composition.

11 Claims, 2 Drawing Sheets
Specification includes a Sequence Listing.

(56) References Cited

U.S. PATENT DOCUMENTS

| | | |
|---|---|---|
| 2011/0237646 A1 | 9/2011 | Smith et al. |
| 2011/0294868 A1 | 12/2011 | Monia |
| 2012/0149109 A1 | 6/2012 | Brown-Driver et al. |
| 2012/0225927 A1 | 9/2012 | Sah et al. |
| 2012/0244207 A1 | 9/2012 | Fitzgerald et al. |
| 2012/0294905 A1 | 11/2012 | Sah et al. |
| 2013/0281510 A1 | 10/2013 | Sah et al. |
| 2016/0076029 A1 | 3/2016 | Sah et al. |
| 2016/0090593 A1 | 3/2016 | Sah et al. |
| 2016/0201058 A1 | 7/2016 | Khvorova et al. |
| 2016/0264963 A1 | 9/2016 | Sah et al. |
| 2017/0096663 A1 | 4/2017 | Sah et al. |

FOREIGN PATENT DOCUMENTS

| | | |
|---|---|---|
| WO | WO 2004/090108 | 10/2004 |
| WO | WO 2005/120152 | 12/2005 |
| WO | WO 2007/012191 | 2/2007 |
| WO | WO 2008/042973 | 4/2008 |
| WO | WO 2009/086558 | 7/2009 |
| WO | WO 2009/127060 | 10/2009 |
| WO | WO 2010/042877 | 4/2010 |
| WO | WO 2010/048228 | 4/2010 |
| WO | WO 2010/053572 | 5/2010 |
| WO | WO 2010/054406 | 5/2010 |
| WO | WO 2010/088537 | 8/2010 |
| WO | WO 2010/129709 | 11/2010 |
| WO | WO 2010/144740 | 12/2010 |
| WO | WO 2010/147992 | 12/2010 |
| WO | WO 2011/056883 | 5/2011 |
| WO | WO 2011/123468 | 10/2011 |

OTHER PUBLICATIONS

Alnylam Pharmaceuticals, "Phase 2 Open-Label Extension Study of Patisiran—An RNAi Therapeutic for the Treatment of Familial Amyloidotic Polyneuropathy," Apr. 22, 2015, 29 pages.

Berk, J. et al., "Repurposing Diflunisal for Familial Amyloid Polyneuropathy: A Randomized Clinical Trial," The Journal of the American Medical Association 310(24), Dec. 25, 2013, pp. 2658-2667.

Coelho, T. et al., "Long-Term Effects of Tafamidis for the Treatment of Transthyretin Familial Amyloid Polyneuropathy," Journal of Neurology 260, Aug. 22, 2013, pp. 2802-2814.

Coelho, T. et al., "Safety and Efficacy of RNAi Therapy for Transthyretin Amyloidosis," The New England Journal of Medicine, Aug. 29, 2013, pp. 819-829.

Dyck, P. et al., "Detection, Characterization, and Staging of Polyneuropathy: Assessed in Diabetics," Muscle Nerve 11(1), Jan. 1988, pp. 21-32.

Dyck, P. et al., "Longitudinal Assessment of Diabetic Polyneuropathy Using a Composite Score in the Rochester Diabetic Neuropathy Study Cohort," Neurology, Jul. 1997, 49, pp. 229-239.

Judge, A., et al., "Confirming the RNAi-mediated mechanism of action of siRNA-based cancer therapeutics in mice," The Journal of Clinical Investigation, 2009, pp. 1-13.

Love, K., et al., "Lipid-like materials for low-dose, in vivo gene silencing," PNAS, Feb. 2, 2010, pp. 1864-1869, vol. 107, No. 5.

Lozeron, P. et al., "Effect on Disability and Safety of Tafamidis in Late Onset of Met30 Transthyretin Familial Amyloid Polyneuropathy," European Journal Neurology 20(12), Dec. 2013, pp. 1539-1545.

Suanprasert, N. et al., "Retrospective Study of a TTR FAP Cohort to Modify NIS + 7 for Therapeutic Trials," Journal of the Neurological Sciences 344, Jun. 27, 2014, pp. 121-128.

Agrawal, S., et al., "Antisense oligonucleotides: towards clinical trials." Trends in Biotechnology. Oct. 1996, vol. 14, pp. 376-387.

Bass, B., "The short answer," Nature, May 24, 2001, pp. 428-429, vol. 411.

Elbashir, S., et al., "Analysis of gene function in somatic mammalian cells using small interfering RNAs," Methods, 2002, pp. 199-213, vol. 26.

Elbashir, S., et al., "Duplexes of 21-nucleotide RNAs mediate RNA interference in mammalian cell culture," Nature, May 24, 2001, p. 494-498, vol. 411.

Elbashir, S., et al., "Functional Anatomy of siRNAs for Mediating Efficient RNAi in *Drosophila melanogaster* Embryo Lysate", The EMBO Journal, 2001, pp. 6877-6888, vol. 20, No. 23.

Elbashir, S., et al., "RNA Interference is Mediated by 21- and 22 Nucleotide RNAs," Genes & Development, 2001, pp. 188-200, vol. 15.

Fire, A., "RNA-triggered Gene Silencing," Trends in Genetics, Sep. 1999, pp. 358-363, vol. 15, No. 9.

Fire, A., et al., "Potent and Specific Genetic Interference by Double Stranded RNA in Caenorhabditis elegans," Nature, Feb. 19, 1998, pp. 806-811, vol. 391.

Hornung, V., et al., "Sequence-specific potent induction of IFN-α by short interfering RNA in plasmacytoid dendritic cells throughTLR7," Nature Medicine, Mar. 2005, pp. 263-270, vol. 11, No. 3.

Reynolds, et al. (2004) "Rational siRNA design for RNA interference," Nature Biotechnology, vol. 22, No. 3, pp. 326-330.

Robbins, M., et al., "Stable expression of shRNAs in human $CD34^+$ progenitor cells can avoid induction of interferon responses to siRNAs in vitro," Nature Biotechnology, May 2006, pp. 566-571, vol. 24, No. 5.

Rose, S., et al., "Functional polarity is introduced by Dicer processing of short substrate RNAs," Nucleic Acids Research, 2005, pp. 4140-4156, vol. 33, No. 13.

Tuschl, T., "Functional genomics: RNA sets the standard," Nature, Jan. 16, 2003, vol. 421, No. 6920, pp. 220-221.

Tuschl T., "RNA Interference and Small Interfering RNAs" Chembiochem, 2001, pp. 239-245, vol. 2.

Tuschl, T., et al., "Small Interfering RNAs: A Revolutionary Tool for the Analysis of Gene Function and Gene Therapy," Molecular Interventions, 2002, pp. 158-167, vol. 2, No. 3.

Tuschl, T., "Mammalian RNA Interference," RNAi, a Guide to Gene Silencing, Chapter 13, G.J. Hannon (ed,), 2003, pp. 265-295.

Tuschl, T., et al., "Targeted mRNA Degradation by Double-Stranded RNA in Vitro," Genes & Development, 1999, pp. 3191-3197, vol. 13.

Tuschl, T., "Expanding small RNA interference," Nature Biotechnology, May 2002, pp. 446-448, vol. 20.

Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.

Weil, et al (2002) "Targeting the Kinesin Eg5 to Monitor siRNA Transfection in Mammalian Cells," *Biotechniques* 33(6):1244-1248.

Zimmerman, et al., "RNAi-mediated gene silencing in non-human primates," Nature, May 4, 2006, pp. 111-114, vol. 441, With supplementary information.

Adams, D et al., "FAP Neuropathy and Emerging Treatments," Current Neurology and Neuroscience Reports, Feb. 1, 2014. vol. 14, No. 3, pp. 1-12.

Almeida, M.-R., et al., "Small Transthyretin (TTR) Ligands as Possible Therapeutic Agents in TTR Amyloidoses," Current Drug Targets—CNS & Neurological Disorders, Oct. 2005, pp. 587-596, vol. 4, No. 5.

Ando, Y., et al., "Pathogenesis and Therapy for Transthyretin Related Amyloidosis," Rinsho byori (The Japanese Journal of Clinical Pathology), Feb. 2008, vol. 56, pp. 114-120 (With English Abstract).

Benson, M., et al., "Targeted suppression of an amyloidogenic transthyretin with antisense oligonucleotides," Muscle & Nerve, 2006, pp. 609-618, vol. 33, No. 5.

Cendron, L., et al., NCBI, "Rattus norvegicus transthyretin (Ttr), mRNA," GenBank Accession No. NM_012681, Feb. 14, 2010, 2 Pages, [online] [Retrieved on Jun. 20, 2011] Retrieved from the internet: <URL: http://www.ncbi.nlm.nih.gov/nuccorel6981683?sat=14&satkey>.

(56) References Cited

OTHER PUBLICATIONS

GenBank Accession No. NM_000371.3, "*Homo sapiens* transthyretin (TTR), mRNA," Sep. 23, 2012, 4 pages.
GenBank Accession No. NM_000371.2, "*Homo sapiens* transthyretin (TTR), mRNA," Dec. 21, 2008, 3 pages.
GenBank Accession No. NM_012681.1, "Rattus norvegicus transthyretin (Ttr), mRNA," Feb. 14, 2010, 3 pages.
GenBank Accession No. NM_013697.2, "Mus musculus transthyretin (Ttr), mRNA," Apr. 5, 2007, 3 pages.
Hara, R., et al., "Impact of Liver Transplantation on Transthyretin-Related Ocular Amyloidosis in Japanese Patients," Arch Ophthalmol, 2010, pp. 206-210, vol. 128, No. 2.
Heyes, J., et al., "Cationic lipid saturation influences intracellular delivery of encapsulated nucleic acids," Journal of Controlled Release, 2005, pp. 276-287, vol. 107.
Kurosawa, T., et al., "Selective silencing of a mutant transthyretin allele by small interfering RNAs" Biochem Biophys Res Commun., 2005, pp. 1012-1018, vol. 337, No. 3.
Maeda, S., "Use of genetically altered mice to study the role of serum amyloid P component in amyloid deposition," Amyloid: Protein Folding Disord., 2003, pp. 17-20, vol. 10, Suppl. 1.
Morsles, S., "Collagen gel contraction by ARPE-19 cells is mediated by a FAK-Src dependent pathway," Experimental Eye Research, 2007, pp. 790-798, vol. 85.
Morrissey, D., et al., "Potent and persistent in vivo anti-HBV activity of chemically modified siRNAs," Nature Biotechnology, 2005, pp. 1002-1007, vol. 23.
Palaninathan, S.K. et al., "*Homo sapiens* transthyretin (Ttr), mRNA," Database GenBank [online], Accession No. NM_000371.2, NCBI, Oct. 5, 2008, 3 pages, [online] [Retrieved on Apr. 15, 2014] Retrieved from the internet <URL:http://www.ncbi.nlm.nih.gov/nuccore/1677363u3 ?sat=12&satkey=87 48419>.
Santos, A. L. G., et al., "Intraocular Delivery of Oligonucleotides," Current Pharmaceutical Biotechnology, 2005, pp. 7-15, vol. 6.
Sekijima, Y., "Recent Progress in the Understanding and Treatment of Transthyretin Amyloidosis," Journal of Clinical Pharmacy and Therapeutics, Jun. 2014. vol. 39, No. 3, pp. 225-233.
Sekijima, Y., et al., "Pathogenesis of and Therapeutic Strategies to Ameliorate the Transthyretin Amyloidoses", Current Pharmaceutical Design, Jan. 1, 2008, pp. 3219-3230, vol. 14, No. 30.
Stein, T., et al., "Neutralization of transthyretin reverses the neuroprotective effects of secreted amyloid precursor protein (APP) in $APP_{sw}$ mice resulting in Tau phosphorylation and loss of Hippocampal neurons: support for the amyloid hypothesis." The Journal of Neuroscience, 2004, p. 7707-7717, vol. 24, No. 35.
Tasaki, M., et al., "siRNA therapy for TTR-related ocular amyloidosis," Amyloid, $12^{th}$ International Symposium on Amyloidosis from Molecular Mechanisms Toward the Cure of Systemic AM, 2010, pp. 52-53, vol. 17, No. Suppl 1.
Tomi, M., "Drug Delivery Targeting the Retina," Journal of Pharmaceutical Science and Technology, Japan, 2003, pp. 193-196, vol. 63, No. 4.
Ueda, M., et al., "A transgenic rat with the human ATTR V30M: a novel tool for analysis of ATTY metabolisms," Biochemical and Biophysical Research Communications, 2006, pp. 299-304, vol. 352.
Yasukawa, T., "New Ocular Drug Delivery Systems," Journal of the Eye, 2010, pp. 1377-1384, vol. 27, No. 10.
Notification of the First Office Action for Chinese Patent Application No. CN200980141740.4, dated Jun. 5, 2012, 6 Pages.
Notification of the Second Office Action for Chinese Patent Application No. CN 200980141740.4, dated Mar. 1, 2013, 8 Pages.
Communication pursuant to Article 94(3) EPC for European Patent Application No. EP 09810834.3, dated Feb. 15, 2012, 6 Pages.
Communication Pursuant to Article 94(3) EPC for European Patent Application No. EP 09810834.3, dated Nov. 9, 2012, 4 Pages.
Examination Report for New Zealand Patent Application No. 592867, dated Jun. 14, 2011, 2 Pages.
PCT International Search Report and Written Opinion, PCT/US2010/055311, dated Mar. 2, 2011, 12 pages.
PCT International Search Report and Written Opinion, PCT/US2009/061381, dated Jul. 26, 2010, 15 pages.
PCT International Search Report and Written Opinion, PCT/US2011/030392, dated Jun. 27, 2011, 10 pages.
PCT Invitation to Pay Additional Fees and, Where Applicable, Protest Fee, PCT/US2009/061381, Apr. 27, 2010, 7 Pages.
PCT International Search Report and Written Opinion for PCT/US15/47185, dated Feb. 9, 2016, 12 Pages.
Supplementary European Search Report for European Patent Application No. EP 11763336, dated Sep. 13, 2013, 11 Pages.
Extended European Search Report for European Patent Application No. EP 10829034.7, dated Aug. 30, 2013, 10 Pages.
Office Action for Japanese Patent Application No. JP 2013-502765, dated Mar. 17, 2015, 5 Pages.
Office Action for Japanese Patent Application No. JP 2011-533279, dated Apr. 22, 2014, 9 Pages.
Office Action for Australian Patent Application No. AU 2009307677, dated May 27, 2014, 6 Pages.
Suhr, O., "Clinical Update on Patisiran Phase 2 Trials in Familial Amyloidotic Polyneuropathy," Alnylam Pharmaceuticals, Apr. 30, 2014, 15 Pages, Retrieved from the Internet on Mar. 8, 2018 at <URL:http://www.alnylam.com/web/assets/ALNY-Clinical-Update-Patisiran-Phase2-Trials-ISA2014.pdf>.
Anonymous: "Clinical Updates on ALN-TTR 1-10Programs Patisiran (ALN-TTR02) and ALN-TTRsc for the Treatment of Transthyretin Amyloidosis", International Symposium on Familial Amyloidotic Polyneuropathy, Alnylam Pharmaceuticals, Nov. 10, 2013, 24 Pages, Retrieved from the Internet on Mar. 8, 2018, at <URL:http://www.alnylam.com/web/assets/ALNY-ISFAP-ALN-TTRprogram-Nov2013.pdf>.
Anonymous: "The Study of an Investigational Drug, ALN-TTR02, for the Treatment of Transthyretin (TTR)—Mediated Amyloidosis," ClinicalTrials.gov, Apr. 15, 2014, 3 Pages, Retrieved from the Internet on Mar. 9, 2018 at <URL:https://web.archive.org/web/20140415012409/https://clinicaltrials.gov/ct2/show/NCT01960348>.
Extended European Search Report for European Patent Application No. EP 15835924.0, dated Mar. 23, 2018, 10 Pages.

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
guaaccaaga guauuccaut t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
auggaauacu cuugguuact t                                              21

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aatcaagtta aagtggaatg aaaagtgcct ttcacag                             37

<210> SEQ ID NO 4
<211> LENGTH: 30
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 4
gcctttcaca ggaatgtttt attgtctctg                                          30

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctctgcctgg acttctaaca tagcatatga ggtg                                     34
```

METHODS OF TREATING TRANSTHYRETIN (TTR) MEDIATED AMYLOIDOSIS

CROSS-REFERENCE TO RELATED APPLICATIONS

This application is the National Stage of International Application No. PCT/US2015/047185, filed Aug. 27, 2015, which claims the benefit of and priority to U.S. Provisional Patent Application No. 62/044,100, filed on Aug. 29, 2014 and to U.S. Provisional Patent Application No. 62/150,596, filed on Apr. 24, 2015, both which are incorporated by reference in their entirety for all purposes.

SEQUENCE LISTING

The instant application contains a Sequence Listing which has been submitted via EFS-Web and is hereby incorporated by reference in its entirety. Said ASCII copy, created on Feb. 28, 2017, is named $30613_{US-CRF}$_sequencelisting.txt, and is 4,096 bytes in size.

BACKGROUND OF THE INVENTION

Transthyretin (TTR) is a tetrameric protein produced primarily in the liver. Mutations in the TTR gene destabilize the protein tetramer, leading to misfolding of monomers and aggregation into TTR amyloid fibrils (ATTR). Tissue deposition results in systemic ATTR amyloidosis (Coutinho et al., Forty years of experience with type I amyloid neuropathy. Review of 483 cases. In: Glenner et al., Amyloid and Amyloidosis, Amsterdam: Excerpta Media, 1980 pg. 88-93; Hou et al., Transthyretin and familial amyloidotic polyneuropathy. Recent progress in understanding the molecular mechanism of neurodegeneration. FEBS J 2007, 274: 1637-1650; Westermark et al., Fibril in senile systemic amyloidosis is derived from normal transthyretin. Proc Natl Acad Sci USA 1990, 87: 2843-2845). Over 100 reported TTR mutations exhibit a spectrum of disease symptoms.

TTR amyloidosis manifests in various forms. When the peripheral nervous system is affected more prominently, the disease is termed familial amyloidotic polyneuropathy (FAP). When the heart is primarily involved but the nervous system is not, the disease is called familial amyloidotic cardiomyopathy (FAC). A third major type of TTR amyloidosis is called leptomeningeal/CNS (Central Nervous System) amyloidosis.

The most common mutations associated with familial amyloid polyneuropathy (FAP) and ATTR-associated cardiomyopathy, respectively, are Val30Met (Coelho et al., Tafamidis for transthyretin familial amyloid polyneuropathy: a randomized, controlled trial. Neurology 2012, 79: 785-792) and Val122Ile (Connors et al., Cardiac amyloidosis in African Americans: comparison of clinical and laboratory features of transthyretin V122I amyloidosis and immunoglobulin light chain amyloidosis. Am Heart J 2009, 158: 607-614).

Current treatment options for FAP focus on stabilizing or decreasing the amount of circulating amyloidogenic protein. Orthotopic liver transplantation reduces mutant TTR levels (Holmgren et al., Biochemical effect of liver transplantation in two Swedish patients with familial amyloidotic polyneuropathy (FAP-met30). Clin Genet 1991, 40: 242-246), with improved survival reported in patients with early-stage FAP, although deposition of wild-type TTR may continue (Yazaki et al., Progressive wild-type transthyretin deposition after liver transplantation preferentially occurs into myocardium in FAP patients. Am J Transplant 2007, 7:235-242; Adams et al., Rapid progression of familial amyloid polyneuropathy: a multinational natural history study Neurology 2015 Aug. 25; 85(8) 675-82; Yamashita et al., Long-term survival after liver transplantation in patients with familial amyloid polyneuropathy. Neurology 2012, 78: 637-643; Okamoto et al., Liver transplantation for familial amyloidotic polyneuropathy: impact on Swedish patients' survival. Liver Transpl 2009, 15:1229-1235; Stangou et al., Progressive cardiac amyloidosis following liver transplantation for familial amyloid polyneuropathy: implications for amyloid fibrillogenesis. Transplantation 1998, 66:229-233; Fosby et al., Liver transplantation in the Nordic countries—An intention to treat and post-transplant analysis from The Nordic Liver Transplant Registry 1982-2013. Scand J Gastroenterol. 2015 June; 50(6):797-808. Transplantation, in press).

Tafamidis and diflunisal stabilize circulating TTR tetramers, which can slow the rate of disease progression (Berk et al., Repurposing diflunisal for familial amyloid polyneuropathy: a randomized clinical trial. JAMA 2013, 310: 2658-2667; Coelho et al., 2012; Coelho et al., Long-term effects of tafamidis for the treatment of transthyretin familial amyloid polyneuropathy. J Neurol 2013, 260: 2802-2814; Lozeron et al., Effect on disability and safety of Tafamidis in late onset of Met30 transthyretin familial amyloid polyneuropathy. Eur J Neurol 2013, 20: 1539-1545). However, symptoms continue to worsen on treatment in a large proportion of patients, highlighting the need for new, disease-modifying treatment options for FAP.

Description of dsRNA targeting TTR can be found in, for example, International patent application no. PCT/US2009/061381 (WO2010/048228) and International patent application no. PCT/US2010/055311 (WO2011/056883).

SUMMARY

Described herein are methods for reducing or arresting an increase in a Neuropathy Impairment Score (NIS) or a modified NIS (mNIS+7) in a human subject by administering an effective amount of a transthyretin (TTR)-inhibiting composition, wherein the effective amount reduces a concentration of TTR protein in serum of the human subject to below 50 µg/ml or by at least 80%. Also described herein are methods for adjusting a dosage of a TTR-inhibiting composition for treatment of increasing NIS or Familial Amyloidotic Polyneuropathy (FAP) by administering the TTR-inhibiting composition to a subject having the increasing NIS or FAP, and determining a level of TTR protein in the subject having the increasing NIS or FAP. In some embodiments, the amount of the TTR-inhibiting composition subsequently administered to the subject is increased if the level of TTR protein is greater than 50 µg/ml, and the amount of the TTR-inhibiting composition subsequently administered to the subject is decreased if the level of TTR protein is below 50 µg/ml. Also described herein are formulated versions of a TTR inhibiting siRNA.

DETAILED DESCRIPTION

Figure 1:
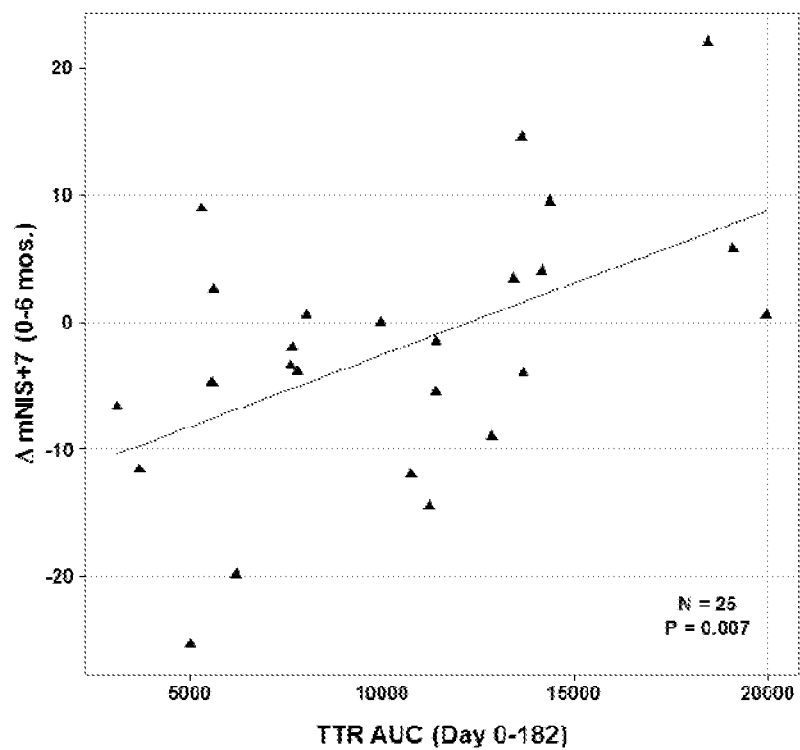
FIG. 1 is a graph illustrating the relationship between progression in ΔNIS or ΔmNIS+7 and TTR concentration.

As described in more detail below, disclosed herein are methods for reducing or arresting an increase in a Neuropathy Impairment Score (NIS) or a modified NIS (mNIS+7) in a human subject by administering an effective amount of a transthyretin (TTR)-inhibiting composition, such that the effective amount reduces a concentration of TTR protein in serum to below 50 μg/ml or by at least 80%. In one embodiment the TTR-inhibiting composition is patisiran. Patisiran is a small interfering ribonucleic acid (siRNA) which is specific for TTR, formulated in a hepatotropic lipid nanoparticle (LNP) for intravenous (IV) administration.

TTR-Inhibiting Compositions

The methods described herein include administration of TTR-inhibiting composition. A TTR-inhibiting composition can be any compound that reduces a concentration of TTR protein in the serum of a human subject. Examples include but are not limited to RNAi, e.g., siRNA. Examples of siRNA include siRNA targeting a TTR gene, e.g., patisirin (described in more detail) below and revusiran. Examples also include antisense RNA. Examples of antisense RNA targeting a TTR gene can be found in U.S. Pat. No. 8,697, 860.

The TTR-inhibiting composition inhibits expression of a TTR gene. As used herein, "transthyretin" ("TTR") refers to a gene in a cell. TTR is also known as ATTR, HsT2651, PALB, prealbumin, TBPA, and transthyretin (prealbumin, amyloidosis type I). The sequence of a human TTR mRNA transcript can be found at NM_000371. The sequence of mouse TTR mRNA can be found at NM_013697.2, and the sequence of rat TTR mRNA can be found at NM_012681.1.

The terms "silence," "inhibit the expression of," "down-regulate the expression of," "suppress the expression of" and the like in as far as they refer to a TTR gene, herein refer to the at least partial suppression of the expression of a TTR gene, as manifested by a reduction of the amount of mRNA which may be isolated from a first cell or group of cells in which a TTR gene is transcribed and which has or have been treated such that the expression of a TTR gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to TTR gene expression, e.g., the amount of protein encoded by a TTR gene which is secreted by a cell, or the number of cells displaying a certain phenotype, e.g., apoptosis. In principle, TTR gene silencing may be determined in any cell expressing the target, either constitutively or by genomic engineering, and by any appropriate assay. However, when a reference is needed in order to determine whether a given dsRNA inhibits the expression of a TTR gene by a certain degree and therefore is encompassed by the instant invention, the assays provided in the Examples below shall serve as such reference.

RNAi

In some embodiments, the methods described herein use a TTR-inhibiting composition that is an RNAi, e.g., an siRNA, e.g., a dsRNA for inhibiting the expression of a TTR gene. In one embodiment, the siRNA is a dsRNA that targets a TTR gene. The dsRNA includes an antisense strand having a region of complementarity which is complementary to at least a part of an mRNA formed in the expression of a TTR gene, and where the region of complementarity is less than 30 nucleotides in length, generally 19-24 nucleotides in length. The dsRNA of the invention can further include one or more single-stranded nucleotide overhangs. TTR-inhibiting siRNAs are described in International patent application no. PCT/US2009/061381 (WO2010/048228) and International patent application no. PCT/US2010/055311 (WO2011/056883), both incorporated by reference herein in their entireties.

In one embodiment, the TTR-inhibiting composition is patisiran, described in more detail below. In another embodiment, the TTR-inhibiting composition is revusiran, an siRNA specific for TTR conjugated to a Trivalent GalNAc carbohydrate cluster. A complete description of revusiran can be found in international application number PCT/US2012/065691 and US Patent Publication No. US20140315835, the contents of which are incorporated by reference in their entirety.

A dsRNA includes two RNA strands that are sufficiently complementary to hybridize to form a duplex structure. One strand of the dsRNA (the antisense strand) includes a region of complementarity that is substantially complementary, and generally fully complementary, to a target sequence, derived from the sequence of an mRNA formed during the expression of a TTR gene, the other strand (the sense strand) includes a region that is complementary to the antisense strand, such that the two strands hybridize and form a duplex structure when combined under suitable conditions. The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus. The term "sense strand," as used herein, refers to the strand of a dsRNA that includes a region that is substantially complementary to a region of the antisense strand. Generally, the duplex structure is between 15 and 80, or 15 and 60 or 15 and 30 or between 25 and 30, or between 18 and 25, or between 19 and 24, or between 19 and 21, or 19, 20, or 21 base pairs in length. In one embodiment the duplex is 19 base pairs in length. In another embodiment the duplex is 21 base pairs in length.

Each strand of a dsRNA is generally between 15 and 80 or 15 and 60 or 15 and 30, or between 18 and 25, or 18, 19, 20, 21, 22, 23, 24, or 25 nucleotides in length. In other embodiments, each is strand is 25-30 nucleotides in length. Each strand of the duplex can be the same length or of different lengths. When two different siRNAs are used in combination, the lengths of each strand of each siRNA can be identical or can differ.

A dsRNA can include one or more single-stranded overhang(s) of one or more nucleotides. In one embodiment, at least one end of the dsRNA has a single-stranded nucleotide overhang of 1 to 4, generally 1 or 2 nucleotides. In another embodiment, the antisense strand of the dsRNA has 1-10 nucleotides overhangs each at the 3' end and the 5' end over the sense strand. In further embodiments, the sense strand of the dsRNA has 1-10 nucleotides overhangs each at the 3' end and the 5' end over the antisense strand.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3, or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding TTR) including a 5' UTR, an open reading frame (ORF), or a 3' UTR. For example, a polynucleotide is complementary to at least a part of a TTR mRNA if the sequence is substantially complementary to a non-interrupted portion of an mRNA encoding TTR.

A dsRNA can be synthesized by standard methods known in the art as further discussed below, e.g., by use of an automated DNA synthesizer, such as are commercially available from, for example, Biosearch, Applied Biosystems, Inc.

Modified dsRNA

In some embodiments, the dsRNA used in the methods described herein is chemically modified to enhance stability. The nucleic acids featured in the invention may be synthesized and/or modified by methods well established in the art, such as those described in "Current protocols in nucleic acid chemistry," Beaucage, S. L. et al. (Eds.), John Wiley & Sons, Inc., New York, N.Y., USA, which is hereby incorporated herein by reference. Specific examples of dsRNA compounds useful in this invention include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; and 5,625,050, each of which is herein incorporated by reference Modified dsRNA backbones that do not include a phosphorus atom therein have backbones that are formed by short chain alkyl or cycloalkyl internucleoside linkages, mixed heteroatoms and alkyl or cycloalkyl internucleoside linkages, or ore or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other suitable dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, a dsRNA mimetic that has been shown to have excellent hybridization properties, is referred to as a peptide nucleic acid (PNA). In PNA compounds, the sugar backbone of a dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Other embodiments of the invention are dsRNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. Also preferred are dsRNAs having morpholino backbone structures of the above-referenced U.S. Pat. No. 5,034,506.

Modified dsRNAs may also contain one or more substituted sugar moieties. Preferred dsRNAs comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred dsRNAs comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an dsRNA, or a group for improving the pharmacodynamic properties of an dsRNA, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxy-alkoxy group. A further preferred modification includes 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$, also described in examples herein below.

Other preferred modifications include 2'-methoxy (2'-$OCH_3$), 2'-aminopropoxy (2'-O$CH_2CH_2CH_2NH_2$) and 2'-fluoro (2'-F). Similar modifications may also be made at other positions on the dsRNA, particularly the 3' position of the sugar on the 3' terminal nucleotide or in 2'-5' linked dsRNAs and the 5' position of 5' terminal nucleotide. DsRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

DsRNAs may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., DsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, each of which is herein incorporated by reference, and U.S. Pat. No. 5,750,692, also herein incorporated by reference.

Patisiran

In one embodiment the TTR-inhibiting composition is patisiran. Patisiran is a small interfering ribonucleic acid (siRNA) which is specific for TTR, formulated in a hepatotropic lipid nanoparticle (LNP) for intravenous (IV) administration (Akinc A, Zumbuehl A, et al. A combinatorial library of lipid-like materials for delivery of RNAi therapeutics. Nat Biotechnol. 2008; 26(5):561-569). This TTR siRNA has a target region within the 3' UTR region of the TTR gene to ensure and confirm homology with WT TTR as well as all reported TTR mutations. Following LNP-mediated delivery to the liver, patisiran targets TTR mRNA for degradation, resulting in the potent and sustained reduction of mutant and WT TTR protein via the RNAi mechanism.

The TTR siRNA (also known as ALN-18328) consists of a sense strand and an antisense strand with the following sequences; the lower case letters indicate 2'-O-methyl versions of the nucleotide:

| Strand | Oligo name | Sequence 5' to 3' | SEQ ID NO: |
|---|---|---|---|
| AD-18328 sense | A-32345 | GuAAccAAGAGuAuuccAudTdT | 1 |
| AD-18328 antisense | A-32346 | AUGGAAuACUCUUGGUuACdTdT | 2 |

The manufacturing process consists of synthesizing the two single strand oligonucleotides of the duplex by conventional solid phase oligonucleotide synthesis. After purification the two oligonucleotides are annealed into the duplex.

The patisiran drug product is a sterile formulation of the TTR siRNA ALN-18328 with lipid excipients (DLin-MC3-DMA, DSPC, cholesterol, and $PEG_{2000}$-C-DMG) in isotonic phosphate buffered saline.

The formulation of patisiran is shown in Table 1 below:

TABLE 1

Composition of Patisiran Drug Product

| Function | Patisiran Component, grade Concentration (mg/mL) |
|---|---|
| Active ingredient | ALN-18328, cGMP 2.0 mg/mL |
| excipient; titratable aminolipid for interaction with the active ingredient | DLin-MC3-DMA (6Z,9Z,28Z,31Z)-heptatriaconta-6,9,28, 31-tetraen-19-yl-4-(dimethylamino) butanoate, cGMP; 12.7 mg/mL |
| excipient; stability of drug product and desired biodistribution | $PEG_{2000}$-C-DMG ((R)-methoxy-$PEG_{2000}$-carbamoyl-di-O-myristyl-sn-glyceride), cGMP; 1.5 mg/mL |
| Structural integrity of LNP particles | DSPC (1,2-Distearoyl-sn-Glycero-3-Phosphocholine), cGMP; 3.1 mg/mL |
| Structural integrity of LNP particles | Cholesterol, synthetic, cGMP; 5.9 mg/mL |
| Buffer | Phosphate buffered saline, cGMP; quantum sufficit |

In some embodiments, the patisiran drug product is provided in a container, e.g., a glass vial, with the following amounts per vial:

TABLE 2

Composition of Patisiran Drug Product including per vial

| Function | Patisiran Component, grade Concentration (mg/mL)/Per vial (mg) |
|---|---|
| Active ingredient | ALN-18328, cGMP 2.0 mg/mL/11.0 mg |
| excipient; titratable aminolipid for interaction with the active ingredient | DLin-MC3-DMA (6Z,9Z,28Z,31Z)-heptatriaconta-6,9,28, 31-tetraen-19-yl-4-(dimethylamino) butanoate, cGMP Mol. wt., 642; 12.7 mg/mL/69.6 mg |
| excipient; stability of drug product and desired biodistribution | $PEG_{2000}$-C-DMG ((R)-methoxy-$PEG_{2000}$-carbamoyl-di-O-myristyl-sn-glyceride), cGMP Mol. wt., 2510; 1.5 mg/mL/8.2 mg |
| Structural integrity of LNP particles | DSPC (1,2-Distearoyl-sn-Glycero-3-Phosphocholine), cGMP Mol. wt., 790; 3.1 mg/mL/17.3 mg |
| Structural integrity of LNP particles | Cholesterol, synthetic, cGMP Mol. wt., 387; 5.9 mg/mL/32.2 mg |
| Buffer | Phosphate buffered saline, cGMP; quantum sufficit |

Patisiran solution for injection contains 2 mg/mL of TTR siRNA drug substance. The patisiran drug product is packaged in 10 mL glass vials with a fill volume of 5.5 mL. The container closure system consists of a United States Pharmacopoeia/European Pharmacopoeia (USP/EP) Type I borosilicate glass vial, a Teflon-faced butyl rubber stopper, and an aluminum flip-off cap.

Tetramer Stabilizers

In some embodiments, the methods described herein include co-administration of a tetramer stabilizer with another TTR-inhibiting composition.

Tetramer stabilizers are compounds that bind to the TTR protein and act to stabilize the TTR tetramer. Mutations that destabilize the TTR tetramer result in misfiled and aggregated TTR.

Examples of tetramer stabilizers include tafamidis and diflunisal. Both tafamidis and diflunisal can slow the rate of disease progression (Berk et al., Repurposing diflunisal for familial amyloid polyneuropathy: a randomized clinical trial. JAMA 2013, 310: 2658-2667; Coelho et al., 2012; Coelho et al., Long-term effects of tafamidis for the treatment of transthyretin familial amyloid polyneuropathy. J Neurol 2013, 260: 2802-2814; Lozeron et al., Effect on disability and safety of Tafamidis in late onset of Met30 transthyretin familial amyloid polyneuropathy. Eur J Neurol 2013, 20: 1539-1545).

Subjects and Diagnosis

Disclosed herein are methods for reducing or arresting an increase in a Neuropathy Impairment Score (NIS) or a modified NIS (mNIS+7) in a human subject, wherein the human subject has a TTR related disorder. In some embodiments, the TTR related disorder is one of the diseases caused by mutations in the transthyretin (TTR) gene. In an embodiment, the disease is TTR amyloidosis, which manifests in various forms such as familial amyloid polyneuropathy (FAP), transthyretin-mediated amyloidosis (ATTR), and symptomatic polyneuropathy. When the peripheral nervous system is affected more prominently, the disease is termed FAP. When the heart is primarily involved but the nervous system is not, the disease is called familial amyloidotic cardiomyopathy (FAC). A third major type of TTR amyloidosis is called leptomeningeal/CNS (Central Nervous System) amyloidosis. ATTR affects the autonomic nervous system.

In some embodiments, the human subject with a TTR related disorder has a mutant TTR gene. Over 100 reported TTR mutations exhibit a spectrum of disease symptoms. The most common mutations associated with FAP and ATTR-associated cardiomyopathy, respectively, are Val30Met and Val122Ile. TTR mutations cause misfolding of the protein and accelerate the process of TTR amyloid formation, and are the most important risk factor for the development of clinically significant TTR amyloidosis (also called ATTR (amyloidosis-transthyretin type)). More than 85 amyloidogenic TTR variants are known to cause systemic familial amyloidosis.

In some embodiments, a human subject is selected to receive treatment for any form of TTR amyloidosis if the human subject is an adult (≥18 years) with biopsy-proven ATTR amyloidosis and mild-to-moderate neuropathy. In a further embodiment, the human subject also has one or more of the following: Karnofsky performance status (KPS) ≥60%; body mass index (BMI) 17-33 kg/m$^2$; adequate liver and renal function (aspartate transaminase (AST) and alanine transaminase (ALT)≤2.5×the upper limit of normal (ULN), total bilirubin within normal limits, albumin>3 g/dL, and international normalized ratio (INR)≤1.2; serum creatinine≤1.5 ULN); and seronegativity for hepatitis B virus and hepatitis C virus.

In another embodiment, a human subject is excluded from treatment if the human subject had a liver transplant; had surgery planned during the treatment; is HIV-positive; had received an investigational drug other than tafamidis or diflunisal within 30 days; had a New York Heart Association heart failure classification >2; is pregnant or nursing; had known or suspected systemic bacterial, viral, parasitic, or fungal infections; had unstable angina, uncontrolled clinically significant cardiac arrhythmia; or had a prior severe reaction to a liposomal product or known hypersensitivity to oligonucleotides.

Neuropathy Impairment Score (NIS)

The methods disclosed herein reduce or arrest an increase in a Neuropathy Impairment Score (NIS) in a human subject by administering a transthyretin (TTR)-inhibiting composition. NIS refers to a scoring system that measures weakness, sensation, and reflexes, especially with respect to peripheral neuropathy. The NIS score evaluates a standard group of muscles for weakness (1 is 25% weak, 2 is 50% weak, 3 is 75% weak, 3.25 is movement against gravity, 3.5 is movement with gravity eliminated, 3.75 is muscle flicker without movement, and 4 is paralyzed), a standard group of muscle stretch reflexes (0 is normal, 1 is decreased, 2 is absent), and touch-pressure, vibration, joint position and motion, and pinprick (all graded on index finger and big toe: 0 is normal, 1 is decreased, 2 is absent). Evaluations are corrected for age, gender, and physical fitness.

In one embodiment, the method for reducing a NIS score results in a reduction of NIS by at least 10%. In other embodiments, the method score results in a reduction of NIS by at least 5, 10, 15, 20, 25, 30, 40, or by at least 50%. In other embodiments, the method arrests an increasing NIS score, e.g., the method results in a 0% increase of the NIS score.

Methods for determining an NIS in a human subject are well known to one of skill in the art and can be found is the following:

Dyck, P J et al., Longitudinal assessment of diabetic polyneuropathy using a composite score in the Rochester Diabetic Neuropathy Study cohort, Neurology 1997. 49(1): pgs. 229-239).

Dyck P J. Detection, characterization, and staging of polyneuropathy: assessed in diabetics. Muscle Nerve. 1988 January; 11(1):21-32.

Modified Neuropathy Impairment Score (mNIS+7)

In some embodiments, the methods disclosed herein reduce or arrest an increase in a modified Neuropathy Impairment Score (mNIS+7) in a human subject by administering a transthyretin (TTR)-inhibiting composition. As well known to one of ordinary skill, mNIS+7 refers to a clinical exam-based assessment of neurologic impairment (NIS) combined with electrophysiologic measures of small and large nerve fiber function (NCS and QST), and measurement of autonomic function (postural blood pressure).

The mNIS+7 score is a modification of the NIS+7 score (which represents NIS plus seven tests). NIS+7 analyzes weakness and muscle stretch reflexes. Five of the seven tests include attributes of nerve conduction. These attributes are the peroneal nerve compound muscle action potential amplitude, motor nerve conduction velocity and motor nerve distal latency (MNDL), tibial MNDL, and sural sensory nerve action potential amplitudes. These values are corrected for variables of age, gender, height, and weight. The remaining two of the seven tests include vibratory detection threshold and heart rate decrease with deep breathing.

The mNIS+7 score modifies NIS+7 to take into account the use of Smart Somatotopic Quantitative Sensation Testing, new autonomic assessments, and the use of compound muscle action potential of amplitudes of the ulnar, peroneal, and tibial nerves, and sensory nerve action potentials of the ulnar and sural nerves (Suanprasert, N. et al., Retrospective study of a TTR FAP cohort to modify NIS+7 for therapeutic trials, J. Neurol. Sci., 2014. 344(1-2): pgs. 121-128).

In an embodiment, the method for reducing an mNIS+7 score results in a reduction of mNIS+7 by at least 10%. In other embodiments, the method score results in a reduction of an mNIS+7 score by at least 5, 10, 15, 20, 25, 30, 40, or by at least 50%. In other embodiments, the method arrests an increasing mNIS+7, e.g., the method results in a 0% increase of the mNIS+7.

Serum TTR Protein Concentration.

The methods described herein include administering to the human subject an effective amount of a transthyretin (TTR)-inhibiting composition, wherein the effective amount reduces a concentration of TTR protein in serum of the human subject to below 50 µg/ml or by at least 80%. The serum TTR protein concentration can be determined directly using any methods known to one of skill in the art, e.g., an antibody based assay, e.g., an ELISAs. Alternatively, the serum TTR protein concentration can be determined by measuring the amount of TTR mRNA. In further embodiments, the serum TTR protein concentration is determined by measuring the concentration of a surrogate, e.g., Vitamin A or retinol binding protein (RBP). In one embodiment, the serum TTR protein concentration is determined using an ELISA assay as described in the Examples below.

In some embodiments, the concentration of serum TTR protein is reduced to below 50 µg/ml, or to below 40 µg/ml, 25 µg/ml, or 10 µg/ml. In some embodiments, the concentration of serum TTR protein is reduced by 80%, or by 81, 82, 83, 84, 85, 86, 87, 88, 89, 90, or by 95%.

AUC

AUC refers to the area under the curve of the concentration of a composition, e.g. TTR, in the plasma of the bloodstream over time after a dose of a drug, e.g., a TTR-inhibiting composition, is administered to a patient. It is affected by the rate of absorption into and the rate of removal of the composition from the patient's blood plasma. As one of skill in the art knows, AUC can be determined by calculating the integral of the plasma composition concentration after the drug is administered. In another aspect, AUC can be predicted using the following formula:

$$\text{Predicted AUC} = (D \times F)/CL$$

where D is the dosage concentration, F is a measure of bioavailability, and CL is the predicted rate of clearance. One of skill in the art appreciates that the values for the predicted AUC have an error in the range of ±3- to 4-fold.

In some embodiments, the data for determining AUC is obtained by taking blood samples from the patient at various time intervals after administration of the drug. In one aspect, the mean AUC in the patient's plasma after administration of the TTR-inhibiting composition is in the range of about 9000 to about 18000.

It is understood that the plasma concentration of TTR, may vary significantly between subjects, due to variability with respect to metabolism and/or possible interactions with other therapeutic agents. In accordance with one aspect of the present invention, the blood plasma concentration of TTR may vary from subject to subject. Likewise, values such as maximum plasma concentration ($C_{max}$) or time to reach maximum plasma concentration ($T_{max}$) or area under the curve from time zero to time of last measurable concentration ($AUC_{last}$) or total area under the plasma concentration time curve (AUC) may vary from subject to subject. Due to this variability, the amount necessary to constitute "a therapeutically effective amount" of a compound, such as, a TTR-inhibiting composition, may vary from subject to subject.

Pharmaceutical Compositions

The methods described herein include administration of a TTR inhibiting composition, e.g., an siRNA targeting a TTR gene, e.g., patisiran. In some embodiments, the TTR inhibiting composition is a pharmaceutical composition.

As used herein, a "pharmaceutical composition" comprises a TTR inhibiting composition and a pharmaceutically acceptable carrier. The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

The pharmaceutical compositions of the present invention may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g., intraparenchymal, intrathecal or intraventricular, administration.

The compositions can be delivered in a manner to target a particular tissue, such as the liver (e.g., the hepatocytes of the liver). Pharmaceutical compositions can be delivered by injection directly into the brain. The injection can be by stereotactic injection into a particular region of the brain (e.g., the substantia nigra, cortex, hippocampus, striatum, or globus pallidus), or the dsRNA can be delivered into multiple regions of the central nervous system (e.g., into multiple regions of the brain, and/or into the spinal cord). The dsRNA can also be delivered into diffuse regions of the brain (e.g., diffuse delivery to the cortex of the brain).

In one embodiment, a dsRNA targeting TTR can be delivered by way of a cannula or other delivery device having one end implanted in a tissue, e.g., the brain, e.g., the substantia nigra, cortex, hippocampus, striatum, corpus callosum or globus pallidus of the brain. The cannula can be connected to a reservoir of the dsRNA composition. The flow or delivery can be mediated by a pump, e.g., an osmotic pump or minipump, such as an Alzet pump (Durect, Cupertino, Calif.). In one embodiment, a pump and reservoir are implanted in an area distant from the tissue, e.g., in the abdomen, and delivery is effected by a conduit leading from the pump or reservoir to the site of release. Infusion of the dsRNA composition into the brain can be over several hours or for several days, e.g., for 1, 2, 3, 5, or 7 days or more. Devices for delivery to the brain are described, for example, in U.S. Pat. Nos. 6,093,180, and 5,814,014.

Dosage and Timing

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the TTR-inhibiting compositions encompassed by the invention can be made using conventional methodologies or on the basis of in vivo testing using an appropriate animal model, as described elsewhere herein.

In general, a suitable dose of a pharmaceutical composition of the TTR-inhibiting composition will be in the range of 0.01 to 200.0 milligrams per kilogram body weight of the recipient per day, generally in the range of 1 to 50 mg per kilogram body weight per day.

For example, the TTR-inhibiting composition can be an siRNA, an can be administered at, 0.01 mg/kg, 0.05 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.628 mg/kg, 2 mg/kg, 3 mg/kg, 5.0 mg/kg, 10 mg/kg, 20 mg/kg, 30 mg/kg, 40 mg/kg, or 50 mg/kg per single dose. In another embodiment, the dosage is between 0.15 mg/kg and 0.3 mg/kg. For example, the TTR-inhibiting composition can be administered at a dose of 0.15 mg/kg, 0.2 mg/kg, 0.25 mg/kg, or 0.3 mg/kg. In an embodiment, the TTR-inhibiting composition is administered at a dose of 0.3 mg/kg.

The pharmaceutical composition (e.g., patisiran) may be administered once daily, or once or twice every 5, 10, 15, 20, 21, 22, 23, 24, 25, 26, 27, 28, 29, or 30 days. The dosage unit can be compounded for delivery over several days, e.g., using a conventional sustained release formulation which provides sustained release of the TTR-inhibiting composition over a several day period. Sustained release formulations are well known in the art and are particularly useful for delivery of agents at a particular site, such as could be used with the agents of the present invention.

In an embodiment, the TTR-inhibiting composition is patisiran, and the dosage is 0.3 mg/kg, and wherein the dose is administered once every 21 days. In another embodiment, the effective amount is 0.3 mg/kg and the effective amount is administered once every 21 days via a 70 minute infusion of 1 mL/min for 15 minutes followed by 3 mL/min for 55 minutes. In another embodiment, the effective amount is 0.3 mg/kg and the effective amount is administered at two doses every 21-28 days via a 60 minute infusion of 3.3 mL/min, or via a 70 minute infusion of 1.1 mL/min for 15 minutes followed by 3.3 mL/min for 55 minutes A dosage of a TTR-inhibiting composition can be adjusted for treatment of increasing NIS or FAP by: administering the TTR-inhibiting composition and determining a level of TTR protein in the subject. If the level of TTR protein is greater than 50 µg/ml, the amount of TTR-inhibiting composition subsequently administered to the subject is increased, and if the level of TTR protein is below 50 μg/ml, the amount of the TTR-inhibiting composition subsequently administered to the subject is decreased.

TTR-inhibiting compositions can be administered in combination with other known agents effective in treatment of pathological processes mediated by target gene expression. In an embodiment, patisiran is administered with a tetramer stabilizer such as tafamidis or diflunisal. In any event, the administering physician can adjust the amount and timing of patisiran and/or tetramer stabilizer administration on the basis of results observed using standard measures of efficacy known in the art or described herein.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992).

Example 1

Safety and Efficacy of Patisiran for TTR Amyloidosis

In a clinical Phase I trial, patisiran was found to reduce TTR levels in patients over a period of 28 days. The results of this study were published in the New England Journal of Medicine (Coelho et al., N Engl J Med 2013; 369:819-29.) The publication is incorporated by reference for all purposes. A summary of study design and results are also presented as follows.

The trial was multicenter, randomized, single-blind, placebo-controlled, and dose-ranging to evaluate the safety and efficacy of a single dose of patisiran in patients with TTR amyloidosis or in healthy adults. Men and women between the ages of 18-45 years were eligible for this trial if they were healthy (as determined on the basis of a medical history, physical examination, and 12-lead electrocardiography), had a BMI of 18.0-31.5, had adequate liver function and blood counts, and did not have childbearing potential.

Series of participants (four in each series) were randomly assigned to receive patisiran at doses of 0.01-0.5 mg/kg or placebo (normal saline) in a 3:1 ratio. The patisiran was administered intravenously during a period of 15 minutes and 60 minutes, respectively. In the trial, patients received similar premedication the evening before and the day of infusion to reduce the risk of infusion-related reactions. These medications included dexamethasone, acetaminophen, diphenhydramine or cetirizine, and ranitidine.

Patisiran pharmacodynamics activity was measured as reflected by serum TTR levels, using a validated enzyme-linked immunosorbent assay (ELISA) for total TTR (Charles River Laboratories, Wilmington Mass.). Baseline levels of TTR, retinol-binding protein, and vitamin A for each patient were defined as the mean of four measurements before the administration of the patisiran. Adverse events were monitored from the start of drug administration through day 28. Safety monitoring also included hematologic evaluations, blood chemical analyses, and thyroid-function tests.

The plasma pharmacokinetics of TTR siRNA contained in patisiran was evaluated by means of a validated ELISA-based hybridization assay. For detection and quantification of siRNA, the ATTO-Probe-HPLC assay (lower limit of quantification, 1.0 ng per milliliter) (Tandem Laboratories, Salt Lake City Utah) was used. WinNonlin (Pharsight, Princeton N.J.) was used to determine the pharmacokinetic estimates.

The knockdown of TTR, vitamin A, and retinol-binding protein was measured as compared with baseline levels. (data not shown).

Results

No significant changes in TTR levels (as compared with placebo) were observed at the two lowest doses of patisiran. However, substantial TTR knockdown was observed in all participants receiving doses of 0.15-0.5 mg/kg (data not shown). TTR knockdown was rapid, potent, and durable across all three dose levels, with highly significant changes, as compared with placebo (P<0.001) through day 28. In light of the robust response seen at 0.15 and 0.3 mg/kg and modest incremental improvement in response at 0.5 mg/kg, only one participant received the dose of 0.5 mg/kg.

There was little variability among participants in the kinetics of response (data not shown), especially at doses of at least 0.3 mg/kg, with more than 50% lowering by day 3, a nadir level by approximately day 10, and continued suppression of more than 50% at day 28, with full recovery occurring by day 70. Maximum values for TTR knockdown for participants receiving 0.15 mg/kg, 0.3 mg/kg, and 0.5 mg/kg were 85.7%, 87.6%, and 93.8%, respectively. The average nadirs at doses of 0.15 mg/kg and 0.3 mg/kg were 82.3% (95% confidence interval (CI), 67.7-90.3) and 86.8% (95% CI, 83.8-89.3), respectively; these nadirs showed little variability among participants when analyzed as either absolute TTR levels or percent TTR knockdown and were highly significant, as compared with placebo (P<0.001) (data not shown).

The degree of knockdown appeared to determine the duration of suppression, with mean reductions at day 28 of 56.6% (95% CI, 11.6-78.7) and 67.1% (95% CI, 45.5-80.1) for participants receiving 0.15 mg/kg and 0.3 mg/kg, respectively, and a 76.8% reduction at day 28 for the single patient receiving 0.5 mg/kg. The TTR knockdown observed in humans at a dose of 0.3 mg/kg was virtually identical to that seen in nonhuman primates at the same dose level (data not shown). These reductions in TTR by patisiran correlated with changes in levels of retinol-binding protein and vitamin A (data not shown).

The use of patisiran did not result in any significant changes in hematologic, liver, or renal measurements or in thyroid function, and there were no drug-related serious adverse events or any study-drug discontinuations because of adverse events (data not shown).

The plasma pharmacokinetic profiles of patisiran showed that the values for the peak plasma concentration and for the area under the curve through the last day for the TTR siRNA increased in an approximately dose-proportional manner over the range of doses that were tested (data not shown).

Specificity of Patisiran

To further demonstrate the specificity of the effect of patisiran, TTR was also measured in a group of healthy volunteers in a phase 1 trial of ALN-PCS, which contains an siRNA targeting PCSK9 (a target for cholesterol lowering) that is formulated in the same type of lipid nanoparticle used in patisiran. A single dose of 0.4 mg/kg ALN-PCS (so-called control siRNA) had no effect on TTR (data not shown), which showed that the effect of patisiran on TTR was due to specific targeting by the siRNA and not a nonspecific effect of the formulation of lipid nanoparticles.

Additional evidence in support of the specificity and mechanism of action of the pharmacodynamics effect of patisiran was obtained using the 5' RACE (rapid amplification of complementary DNA ends) assay on blood samples obtained from participants receiving a dose of 0.3 mg/kg to detect the predicted TTR mRNA cleavage product in circulating extracellular RNA. To collect the blood samples, serum was collected after centrifuging clotted blood sample (pre-dose and at 24 hours post-dose from subjects) at 1200×g for 20 minutes. Serum was centrifuged a second time at 1200×g for 10 minutes to remove floating cellular material and was then frozen. Thawed serum was mixed with lithium chloride (final concentration 1M) and incubated at 4 degrees C. for 1 hour. Samples were spun at 120,000×g for 2 hours at 4 degrees C. to pellet RNA, and total RNA was isolated from pellets by Trizol extraction (Life Technologies, Grand Island, N.Y., USA) and isopropanol precipitation.

To detect the TTR siRNA-mediated cleavage product, the isolated RNA was used for ligation-mediated RACE PCR using the GeneRacer kit (Life Technologies). RNA was ligated to GeneRacer adapter and reverse transcribed using the TTR-specific reverse primer (5'-aatcaagttaaagtggaat-gaaaagtgcctttcacag-3') (SEQ ID NO:3) followed by 2 rounds of PCR using the Gene Racer GR5' forward primer complementary to the adaptor and the TTR-specific reverse primer (5'-gcctttcacaggaatgttttattgtctctg-3')) (SEQ ID NO:4). The nested PCR was carried out with GR5' nested primer and the TTR-specific reverse nested primer (5'-ctctgcctggact-tctaacatagcatatgaggtg-3')) (SEQ ID NO:5). PCR products were cloned using TOPO-Blunt vector (Life Technologies). The cloned inserts were amplified by colony PCR using M13 forward and reverse primers. The amplicons were sequenced with T7 promoter primer at Macrogen sequencing facility. Sequences from 96 clones were aligned to human TTR using CLC WorkBench.

TTR mRNA was detected both in predose samples and in samples obtained 24 hours after drug administration. Consistent with the RNAi mechanism, the predicted mRNA cleavage product was absent in the predose samples and present in postdose samples in all three participants (data not shown).

A LC/MS/MS assay for the quantification of wild type and mutant TTR in human serum was qualified and conducted by Tandem Labs. The serum samples were digested using chymotrypsin and then processed by protein precipitation extraction prior to analysis by LC/MS/MS. The chymotryptic peptides TTRW-1 representing wild type TTR and V30M-1 representing mutant V30M were monitored according to their unique specific mass-to-charge ratio transitions. Standard calibration curve data obtained using stable isotope-labeled peptides (TTRW-1-D8 and V30M-1-D8) were used to calculate endogenous peptide fragments (TTRW-1 and V30M-1) in human serum samples. Peak area ratios for the standards (i.e. TTRW-1-D8 over the internal standard TTRW-L1-D16 and V30M-1-D8 over V30M-L1-D16) were used to create a linear calibration curve using 1/x2 weighted least-squares regression analysis. The qualified LC/MS/MS method achieved a lower limit of quantitation (LLOQ) of 5 ng/ml with standard curves ranging from 5 to 2500 ng/ml.

Example 2

Multi-Dose Study for Safety and Efficacy of Patisiran Therapy for Familial Amyloid Polyneuropathy In this clinical Phase II trial, multiple doses of patisiran were administered to patients with TTR-mediated FAP to evaluate the safety, tolerability, pharmacokinetics, and pharmacodynamics of multiple ascending intravenous doses of patisiran in these patients. This data was presented at the International Symposium on Familial Amyloidotic Polyneuropathy (ISFAP) held in November 2013.

Eligible patients were adults (≥18 years) with biopsy-proven ATTR amyloidosis and mild-to-moderate neuropathy; Karnofsky performance status (KPS)≥60%; body mass index (BMI) 17-33 kg/m$^2$; adequate liver and renal function (aspartate transaminase (AST) and alanine transaminase (ALT)≤2.5×the upper limit of normal (ULN), total bilirubin within normal limits, albumin>3 g/dL, and international normalized ratio (INR)≤1.2; serum creatinine≤1.5 ULN); and seronegativity for hepatitis B virus and hepatitis C virus. Patients were excluded if they had a liver transplant; had surgery planned during the study; were HIV-positive; had received an investigational drug other than tafamidis or diflunisal within 30 days; had a New York Heart Association heart failure classification >2; were pregnant or nursing; had known or suspected systemic bacterial, viral, parasitic, or fungal infections; had unstable angina, uncontrolled clinically significant cardiac arrhythmia; or had a prior severe reaction to a liposomal product or known hypersensitivity to oligonucleotides.

This was a multi-center, international, open-label, multiple dose escalation Phase II study of patisiran in patients with FAP. Cohorts of 3 patients received two doses of patisiran, with each dose administered as an intravenous (IV) infusion. Cohorts 1-3 received two doses of patisiran 0.01, 0.05 and 0.15 mg/kg every four weeks (Q4W), respectively; cohorts 4 and 5 both received two doses of patisiran 0.3 mg/kg Q4W. All patients in cohorts 6-9 received two doses of patisiran 0.3 mg/kg administered every three weeks (Q3W). All patients received premedication prior to each patisiran infusion consisting of dexamethasone, paracetamol (acetaminophen), an H2 blocker (e.g., ranitidine or famotidine), and an H1 blocker (e.g., cetirizine, hydroxyzine or fexofenadine) to reduce the risk of infusion-related reactions. Patisiran was administered IV at 3.3 mL/min over 60 minutes, or over 70-minute using a micro-dosing regimen (1.1 mL/min for 15 minutes followed by 3.3 mL/min for the remainder of the dose).

Serum levels of total TTR protein were assessed for all patients using an enzyme-linked immunosorbent assay (ELISA). Additionally, wild-type and mutant TTR protein were separately and specifically measured in serum for patients with the Val30Met mutation using a proprietary mass spectrometry method (Charles River Laboratories, Quebec, Canada). Serum samples were collected at screening, and on Days: 0, 1, 2, 7, 10, 14, 21, 22, 23 (Q3W only); 28, 29 (Q4W only); 30 (Q4W only); 31 (Q3W only); 35, 38 (Q4W only) and 42, 49, 56, 112 and 208 of follow-up.

Plasma concentration-time profiles were created for TTR siRNA, based on blood samples collected on Day 0 and at the following time points: pre-dose (within 1 hour of planned dosing start), at end of infusion (EOI), at 5, 10 and 30 minutes and at 1, 2, 4, 6, 24, 48, 168, 336, 504 (Day 21, Q3W regimen only) and 672 (Day 28, Q4W regimen only) hours post-infusion. Additional samples were collected on Days 84 and 180 for the Q4W regimens, and on Days 35, 91 and 187 for the Q3W regimen. For cohorts 3-9, blood samples on Day 0 at EOI and 2 hours post-infusion were also analyzed for both free and encapsulated TTR siRNA. Serum TTR siRNA was analyzed using a validated ATTO-Probe high-performance liquid chromatography (HPLC) assay (Tandem Laboratories, Salt Lake City, Utah, USA). PK analyses were conducted using non-compartmental and/or compartmental evaluation of TTR siRNA plasma concentration-time data to determine PK parameter estimates using the validated software program WinNonlin®. Urine samples were analyzed for levels of excreted TTR siRNA, and renal clearance ($CL_R$) was measured after dosing.

Serum levels of vitamin A and retinol binding protein (RBP) were measured by HPLC and nephelometry, respectively, at the same time points specified for total TTR (Biomins Specialized Medical Pathology, Lyon, France).

Means and variances for TTR knockdown from baseline were calculated for the PP population, with baseline defined as the average of all pre-dose values. Analysis of variance (ANOVA) and analysis of covariance (ANCOVA) were used to analyze the PD data (natural log transformed TTR relative to baseline), with Tukey's post hoc tests of individual pairwise comparisons (between dose levels). Nadir TTR levels were defined as the minimum level per patient during the 28-day period (21-day period for Q3W group) after each dose administration (first dose, second dose periods: Days 1-28, 29-56 and Days 1-21, 22-42 for Q4W and Q3W groups, respectively). Relationships between TTR and RBP or vitamin A, relative to baseline, and the relationship between wild-type and V30M TTR levels, were explored via linear regression. The dose-proportionality of the patisiran component in PK parameters was evaluated using a power model analysis. AEs were coded using the Medical Dictionary for Regulatory Activities (MedDRA) coding system, version 15.0, and descriptive statistics provided for AEs, laboratory data, vital signs data, and ECG interval data. All statistical analyses were performed using SAS software, version 9.3 or higher. Efficacy and pharmacodynamics: mean (SD) baseline serum TTR protein levels were similar across the dose cohorts: 272.9 (98.86), 226.5 (12.67), 276.1 (7.65), 242.6 (38.30) and 235.5 (44.45) µg/mL for the 0.01, 0.05, 0.15, 0.3 Q4W and 0.3 mg/kg Q3W dosage groups, respectively.

In comparison to the 0.01 mg/kg dose cohort, a significant reduction in TTR ($p<0.001$ by post hoc tests after ANCOVA) was observed after the first and second doses of patisiran in the 0.3 mg/kg Q4W and Q3W cohorts. (data not shown) In patients with the Val30Met mutation, a very similar degree of knockdown was observed for wild-type and mutant TTR (data not shown). The level of serum TTR knockdown was highly correlated with the reduction in circulating level of RBP ($r^2=0.89$, $p<10^{-15}$) and vitamin A ($r^2=0.90$, $p<10^{-15}$) (data not shown).

Although patients taking tafamidis or diflunisal had significantly increased baseline levels of serum TTR compared with patients not taking stabilizer therapy ($p<0.001$ by ANOVA) (data not shown), patisiran administration resulted in a similar degree of TTR knockdown in these two patient groups (data not shown).

Pharmacokinetics: mean concentrations of the patisiran TTR siRNA component decreased after EOI (data not shown), and there was no accumulation of siRNA following the second dose on Day 21/28. Measurements of encapsulated versus un-encapsulated concentrations of TTR siRNA after each dose indicated stability of the circulating LNP formulation. For both the first and second doses, the mean values for maximum plasma concentration (Cmax) and area under the plasma concentration-time curve from zero to the last measurable time point (AUC0-last) increased in a dose-proportional manner over the dose range tested. Cmax and AUC0-last after dose 1 and dose 2 were comparable, with no accumulation. The median terminal half-life of patisiran at Days 0 and Days 21/28 was 39-59 hours at doses >0.01 mg/kg, and was relatively unchanged when comparing dose 1 and dose 2 for each dose cohort.

These Phase II data demonstrate that treatment of patients with FAP with patisiran led to robust, dose-dependent, and statistically significant knockdown of serum TTR protein levels. Mean sustained reduction in TTR of >80% was achieved with two consecutive doses of patisiran 0.3 mg/kg dosed every 3-4 weeks, with a maximum knockdown of 96% achieved in the Q3W group. These knockdown rates are consistent with the rates observed in the single ascending dose, placebo-controlled Phase 1 study of patisiran (Coelho et al. 2013a). Evidence from other systemic amyloidotic diseases indicates that as little as 50% reduction of the disease-causing protein can result in clinical disease improvement or stabilization (Lachmann et al. 2003; Lachmann et al. 2007). The degree of TTR knockdown with patisiran was not affected by patients taking tafamidis or diflunisal, suggesting that these TTR stabilizer drugs do not interfere with the pharmacologic activity of patisiran. In patients with the Val30Met mutation, patisiran suppressed production of both mutated and wild-type TTR; the latter remains amyloidogenic in patients with late-onset FAP after liver transplantation (Yazaki et al, 2003; Liepnieks et al, 2010).

Example 3

Reduction of Neurological Impairment as Measured by NIS and mNIS+7 by Administering Patisiran An Open Label Extension study was and is performed with FAP patients using the protocols described in Example 2. Administration of patisiran led to a reduction of both NIS and mNIS+7.

FAP patients previously dosed on Phase 2 trial were eligible to roll over onto Phase 2 OLE study. Up to 2 years of dosing were and are performed, 0.30 mg/kg every 3 weeks, with clinical endpoints evaluated every 6 months. The study objectives included effects on neurologic impairment (mNIS+7 and NIS), quality of life, mBMI, disability, mobility, grip strength, autonomic symptoms, nerve fiber density in skin biopsies, cardiac involvement (in cardiac subgroup), and serum TTR levels.

Patient demographics are shown below.

| Characteristic | Result |
|---|---|
| Number of patients | N = 27 (includes 11 patients in cardiac subgroup) |
| Median age | 64.0 years (range 29-77) |
| Gender | 18 males, 9 females |
| TTR genotype | Val30Met (V30M) = 20   Tyr116Ser (Y116S) = 1 |
| | Ser77Tyr (S77Y) = 2   Phe64Leu (F64L) = 1 |
| | Ser77Phe (S77F) = 2   Arg54Thr (R54T) = 1 |
| FAP stage/PND score | Stage 1: 24   I: 14 |
| | Stage 2: 3   II: 10 |
| | IIIa: 2 |
| | IIIb: 1 |
| Concurrent tetramer stabilizer use at baseline | 13 tafamidis, 7 diflunisal, 7 none |
| Current tetramer stabilizer use[1] | 12 tafamidis, 6 diflunisal, 9 none |
| Total doses administered | 511 |
| Median doses/patient to date | 19 (range 13-24) |
| Mean treatment duration | 12.9 months (range 8.4-16.7) |

Baseline characteristics included the following:

| Characteristic | N | Mean (range) |
|---|---|---|
| mNIS+7a (max impairment: 304) | 27 | 52.9 (2.0-122.5) |
| NIS (max impairment: 244) | 27 | 34.8 (4.0-93.4) |

As shown in the table below, administration of patisiran resulted in lowering of serum TTR levels. Patisiran achieved sustained serum TTR lowering of approximately 80%, with further nadir of up to 88% between doses.

| Day | N | Mean % Knockdown |
|---|---|---|
| 1 | 25 | 21.4 |
| 3 | 25 | 46.8 |
| 7 | 25 | 71.1 |
| 17 | 24 | 77.8 |
| 84 | 26 | 78.1 |
| 168 | 27 | 80.5 |
| 182 | 27 | 87.7 |
| 231 | 25 | 82.4 |
| 234 | 24 | 87.0 |
| 238 | 24 | 88.1 |
| 248 | 25 | 86.0 |
| 273 | 22+ | 80.7 |
| 357 | 22 | 81.3 |
| 371 | 18 | 87.1 |
| 462 | 3 | 79.2 |

As shown in the table below, administration of patisiran resulted in a change in mNIS+7 as measured at 6 and 12 months.

| mNIS+7 component | Change from Baseline to Month 6 (n = 27) | | Change from Baseline to Month 12 (n = 20) | |
|---|---|---|---|---|
| | Mean (SEM) | Median (min, max) | Mean (SEM) | Median (min, max) |
| Total | −1.4 (2.06) | −2 (−25.38, 22) | −2.5 (2.85) | −1.5 (−29.75, 24) |
| NIS-weakness | 0.2 (1.17) | 0 (−9.88, 16) | −0.5 (0.86) | 0 (−10.38, 6) |
| NIS-reflexes | −0.7 (0.49) | 0 (−8, 3) | 0.6 (0.43) | 0 (−5.5, 4) |
| QST[#] | −1.1 (1.49) | −1.5 (−15, 16) | −2.6 (2.35) | −2 (−23, 19) |
| NCS Σ5 | 0.2 (0.13) | 0 (−1.5, 1.5) | −0.1 (0.25) | 0 (−2, 3.5) |
| Postural BP[+] | 0 (0.08) | 0 (−1, 1) | −0.1 (0.11) | 0 (−1.5, 05) |

As shown in the table below, administration of patisiran resulted in changes in NIS at 6 and 12 months.

| NIS component | Change from Baseline to Month 6 (n = 27) | | Change from Baseline to Month 12 (n = 20) | |
|---|---|---|---|---|
| | Mean (SEM) | Median (range) | Mean (SEM) | Median (range) |
| Total | −0.7 (1.3) | −1.0 (−12.9, 12) | 0.4 (1.2) | −0.8 (−8.4, 11) |
| NIS-weakness | 0.2 (1.2) | 0 (−9.9, 16) | −0.5 (0.9) | 0 (−10.4 6) |
| NIS-reflexes | −0.7 (0.5) | 0 (−8, 3) | 0.6 (0.44) | 0 (−5.5, 4) |
| NIS-sensation | −0.3 (0.7) | 0 (−9.5, 5) | 0.4 (0.8) | 0.5 (−5, 8) |

Figure 2:
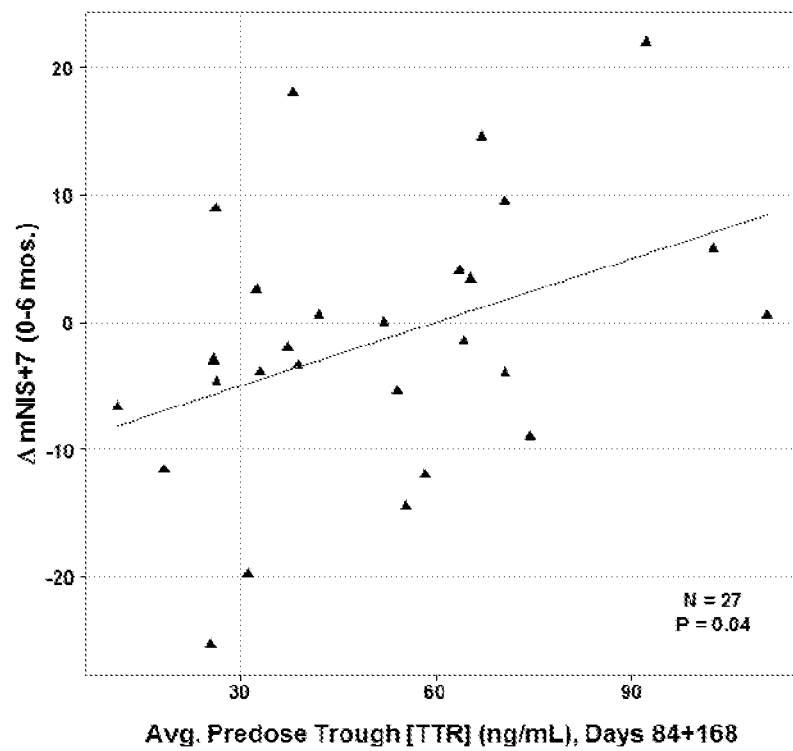
FIG. 2 is a graph illustrating the relationship between progression in ΔNIS or ΔmNIS+7 and TTR concentration.

The relationship between progression in ΔNIS or ΔmNIS+7 and TTR concentration was explored via linear regression as shown in FIG. 1 and FIG. 2. TTR and average pre-dose trough [TTR] correlated with a change in mNIS+7 at 6 months.

NIS and mNIS+7 were measured at 0, 6, and 12 months. ΔNIS or ΔmNIS+7 from 0 to 6 and 0 to 12 months were used as response variables. Predictor variables included two different measures of TTR concentration: TTR protein concentration area under the curve ("AUC"), and average percent knockdown relative to baseline at Days 84 and 168 (for 0-6 month comparisons) and Days 84, 168, 273, and 357 (for 0-12 month comparisons).

For both TTR measures, "baseline" was defined as the average of all pre-dose values. TTR AUC was calculated using raw TTR concentrations (μg/mL) and the method of trapezoids, beginning at baseline value (inserted at Day 0) and extending to Day 182 (for 0-6 month comparisons) or Day 357 (for 0-12 month comparisons). Percent knockdown relative to baseline was calculated at each scheduled timepoint. Linear regression was performed and P values associated with the test of the null hypothesis that no association exists between predictor and response variable were reported.

There was a mean change in mNIS+7 and NIS of −2.5 and 0.4 points, respectively, at 12 months compares favorably to the rapid increase (e.g., 10-18 point increase) in mNIS+7 and NIS estimated at 12 months from prior FAP studies in a patient population with similar baseline NIS. The favorable impact of patisiran on neuropathy impairment score progression correlated with extent of TTR lowering. This demonstrates that a reduction in serum TTR burden by patisiran leads to a clinical benefit in FAP patients.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A method of treating polyneuropathy in a patient with hereditary transthyretin-mediated amyloidosis (hATTR), the method comprising administering a dose of patisiran with a formulation as described in Table 1 to the patient, wherein the dose is 0.3 mg siRNA per kg body weight, and the patisiran is administered via IV infusion once every three weeks, and the patient receives a premedication before infusion to reduce the risk of infusion-related reactions, whereby the method reduces a Neuropathy Impairment Score (NIS) or a modified NIS (mNIS+7) or arrests an increase in a NIS or a mNIS+7 in the patient.

2. The method of claim 1, wherein the patient receives the premedication on the evening before and the day of infusion.

3. The method of claim 1, wherein the premedication comprises dexamethasone, acetaminophen, diphenhydramine, and ranitidine.

4. The method of claim 1, wherein the premedication comprises dexamethasone, acetaminophen, cetirizine, and ranitidine.

5. The method of claim 1, wherein the premedication comprises dexamethasone, paracetamol (acetaminophen), an H2 blocker and an H1 blocker.

6. The method of claim 5, wherein the H2 blocker is ranitidine or famotidine.

7. The method of claim 5, wherein the H1 blocker is cetirizine, hydroxyzine or fexofenadine.

8. The method of claim 1, wherein the patisiran is administered via a 70 minute infusion of 1 mL/min for 15 minutes followed by 3 mL/min for 55 minutes.

9. The method of claim 1, wherein the patisiran is administered via a 70 minute infusion of 1 mL/min for 15 minutes followed by 3 mL/min for 55 minutes and the premedication comprises dexamethasone, paracetamol (acetaminophen), an H2 blocker and an H1 blocker.

10. The method of claim 1, wherein the patient has cardiomyopathy.

11. The method of claim 1, wherein the patient does not have cardiomyopathy.

* * * * *